United States Patent
Bevilacqua et al.

(10) Patent No.: US 6,884,818 B1
(45) Date of Patent: Apr. 26, 2005

(54) PHARMACEUTICAL COMPOSITIONS CONTAINING 8-CHLORO-3 (β-DIETHYLAMINOETHYL)-4-METHYL-7-ETHOXYCARBONYLMETHOXY COUMARIN BASE AND THE SALTS THEREOF WITH CHOLESTEROL-LOWERING ACTIVITY

(75) Inventors: Carla Bevilacqua, Montegrotto Terme (IT); Giuseppe Di Sante, Cadoneghe (IT); Mario Finesso, Montegrotto Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 231 days.

(21) Appl. No.: 10/009,689

(22) PCT Filed: Jun. 13, 2000

(86) PCT No.: PCT/EP00/05383

§ 371 (c)(1),
(2), (4) Date: Mar. 26, 2002

(87) PCT Pub. No.: WO00/76498

PCT Pub. Date: Dec. 21, 2000

(30) Foreign Application Priority Data

Jun. 14, 1999 (IT) .......................... PD99A0128

(51) Int. Cl.$^7$ ................................. A61K 31/35
(52) U.S. Cl. ......................................... 514/457
(58) Field of Search ......................... 514/457

(56) References Cited

U.S. PATENT DOCUMENTS

| 4,349,566 A | 9/1982 | della Valle |
| 4,362,741 A | 12/1982 | della Valle |

FOREIGN PATENT DOCUMENTS

| EP | 0 553 590 A1 | 8/1993 |

OTHER PUBLICATIONS

Hoult J et al, Gen. Pharmac. 27 (4) 713–722, 1996.*

* cited by examiner

*Primary Examiner*—Rebecca Cook
(74) *Attorney, Agent, or Firm*—Birch, Stewart, Kolasch & Birch, LLP

(57) ABSTRACT

The present invention concerns the use of cloricromene (8-chloro-3(β-diethylaminoethyl)-4-methyl-7-ethoxycarbonylmethoxy coumarin) base and the salts thereof to prepare pharmaceutical compositions with cholesterol-lowering activity.

6 Claims, 3 Drawing Sheets

PHARMACEUTICAL COMPOSITIONS CONTAINING 8-CHLORO-3 (β-DIETHYLAMINOETHYL)-4-METHYL-7-ETHOXYCARBONYLMETHOXY COUMARIN BASE AND THE SALTS THEREOF WITH CHOLESTEROL-LOWERING ACTIVITY

This application is the national phase under 35 U.S.C. § 371 of PCT International Application No. PCT/EP00/05383 which has an International filing date of Jun. 13, 2000, which designated the United States of America and was published in English.

SUBJECT OF THE INVENTION

The present invention concerns the use of cloricromene (8-chloro-3(β-diethylaminoethyl)-4-methyl-7-ethoxycarbonylmethoxy coumarin) base and the salts thereof to prepare pharmaceutical compositions with cholesterol-lowering activity.

FIELD OF THE INVENTION

Coumarins include a vast class of phenol substances found in plants, and they are constituted by a benzene ring and an α-pyrone ring fused together.

At least 1,300 coumarins have been identified to date, mainly as metabolites of green plants, in fungi and bacteria.

Cloricromene belongs to the coumarin family and is prepared by the process described in U.S. Pat. Nos. 4,296,039 and 4,452,811 by the Applicant. Its formula is

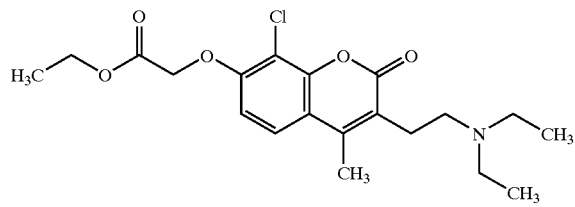

The selective insertion of a chlorine atom in position 8 of the coumarin gives the molecule a coronary vasodilatory property, an antiarhythmic activity (U.S. Pat. No. 4,349,566) and an anti-platelet-aggregation activity (U.S. Pat. No. 4,302,741); see also "The Merck Index", twelfth Edition, 2467.

It has now surprisingly been found that cloricromene can also be used as a cholesterol-lowering agent. Data in the literature indicate a cholesterol-lowering effect of a coumarin derivative of vegetable origin demonstrated on a single experimental model (Huang et al.: British Journal of Pharmacology 1993: 110: 1508–1514; Chen et al.: Morphological evidence for the antiatherogenic effect of scoparone of formula

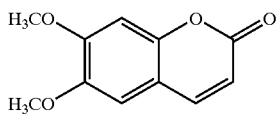

in hyperlipidaemic diabetic rabbits. Cardiovascular Research 1994: 28: 1679–1685).

It is known that high plasma values of total cholesterol or cholesterol bound to the low density lipoprotein represent a major risk factor in arteriosclerotic phenomena responsible for most cases of myocardial or cerebral infarct.

In particular, when plasma cholesterol levels rise above 220 mg/dl, a marked increase in myocardial infarct has been observed.

High cholesterol levels are often seen in patients suffering from vascular diseases caused, for example, by old age, obesity or cardiac disorders.

The first step in treatment for all kinds of hyperlipoproteinaemia is to prescribe a diet to maintain normal body weight and to decrease the lipid concentration in the plasma.

Moreover, dyslipidaemic individuals should keep all other risk factors that might accelerate the arteriosclerotic process to a minimum, by treating hypertension, keeping in check their blood glucose levels in the case of diabetics, giving up smoking and taking plenty of physical exercise.

Lastly, the therapeutic strategy for hyperlipoproteinaemia consists in administering drugs able to reduce the plasma concentration of lipoproteins, reducing their production or increasing their elimination from the plasma.

Of the drugs that reduce the concentration of lipoproteins in the plasma, we name nicotinic acid, clofibrate, gemfibrozil, probucol and resins that scavenge bile acids such as cholestyramine and colestipol, and simvastatin.

Unfortunately, said drugs cause various side effects such as intense hot flushes, itching, peptic ulcers, hyperpigmentation of the skin, nausea, vomiting, hair loss, weakness, impotence and gastrointestinal disorders. Unlike these drugs, cloricromene can be administered over long periods of time without causing any side effects. Lastly, there are no tolerability data to support the use of scoparone in cholesterol-lowering therapies in humans, because the molecule has not been assessed in clinical trials of any kind.

DETAILED DESCRIPTION OF THE INVENTION

It has been found, surprisingly, that cloricromene is able to reduce cholesterol levels in the blood, and it can therefore be used to advantage in the preparation of pharmaceutical compositions with cholesterol-lowering activity.

This activity has proved to be particularly marked in patients suffering from vascular disorders and/or cholesterol levels of over 190 mg/dl.

Test to Compare the Tolerability and Cholesterol-Lowering Effect of Cloricromene and Scoparone in Experimental Models in Rabbit Test No. 1

A preliminary experiment was performed to assess the ability of cloricromene to reduce plasma levels of cholesterol and triglycerides in rabbits fed on a high-fat diet, treated chronically for 4–5 weeks. As reference product we used scoparone, as it is the only coumarin derivative of vegetable origin with a documented effect on these parameters.

The experimental model induces high levels of cholesterol and triglycerides in the plasma by a 1% cholesterolenriched diet, simultaneously inducing diabetes by injection of alloxan, a highly toxic product for the β cells of the pancreas. In this way, it is possible to reach very high values of cholesterol and triglycerides in the system rapidly. The body weight of the animals and the plasma levels of the test parameters were assessed weekly throughout the experiment. The results of this preliminary experiment indicate that the group of rabbits treated with cloricromene present a body weight increase curve which is superimposable on that of the control group of animals, which had diabetes and hypercholesterolaemia but were not receiving any pharmacological treatment. Conversely, in the group of animals treated with scoparone, a marked and progressive reduction in body weight was observed in the animals, which indicated beyond doubt poor tolerability of the pharmacological treatment. The plasma levels of cholesterol and triglycerides too tended to be lower in the group treated with cloricromene than in the group treated with scoparone.

Figure 1:
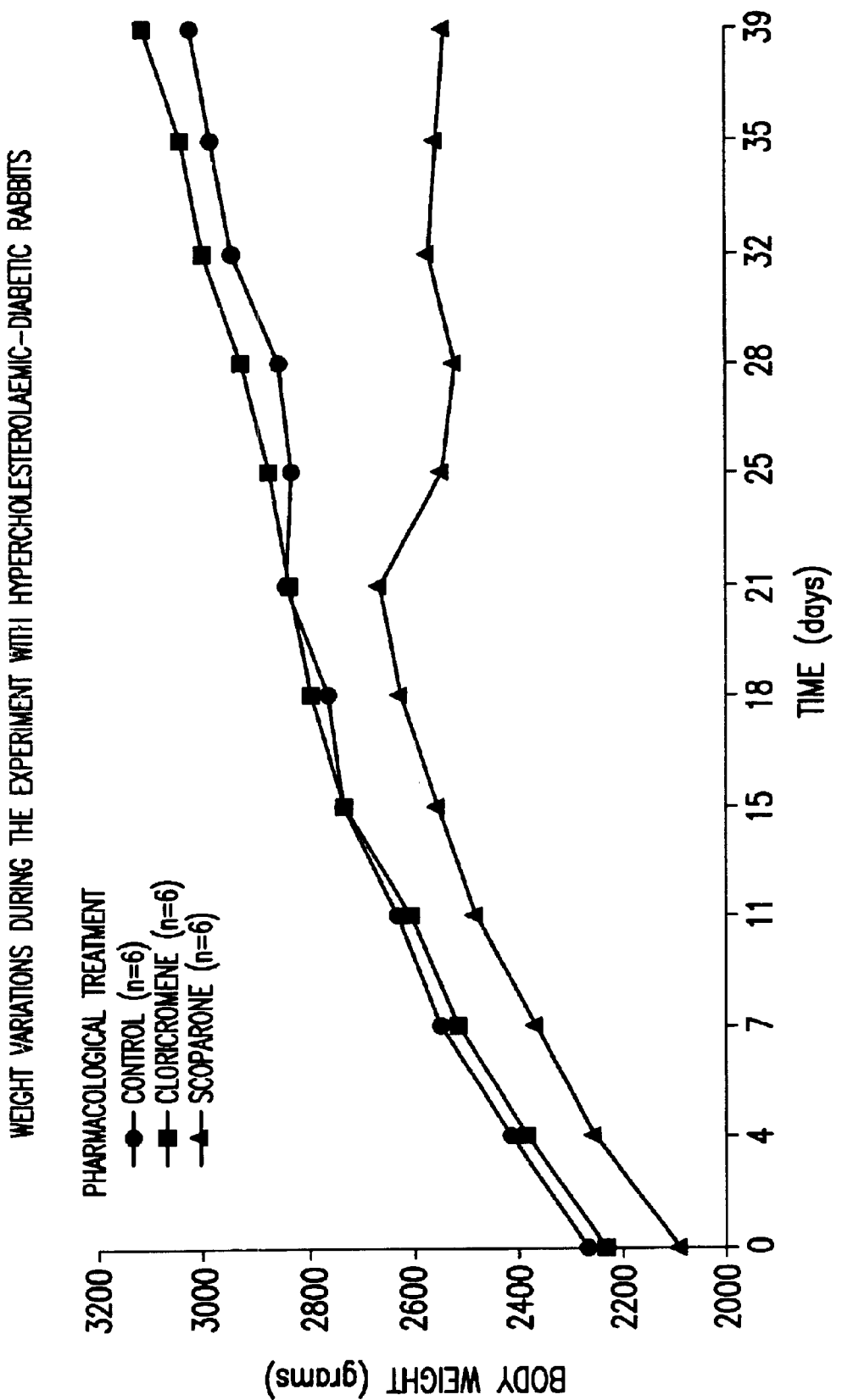
FIG. 1 shows weight variations of rabbits during an Experiment with hypercholesterolaemic-diabetic rabbits wherein the rabbits are treated with cloricromene or scoparone.

The results are reported in FIG. 1.

These data highlight, in comparison to scoparone, cloricromene's absolute lack of toxic activity even when administered repeatedly over long periods of time.

Test No. 2

Figure 2:
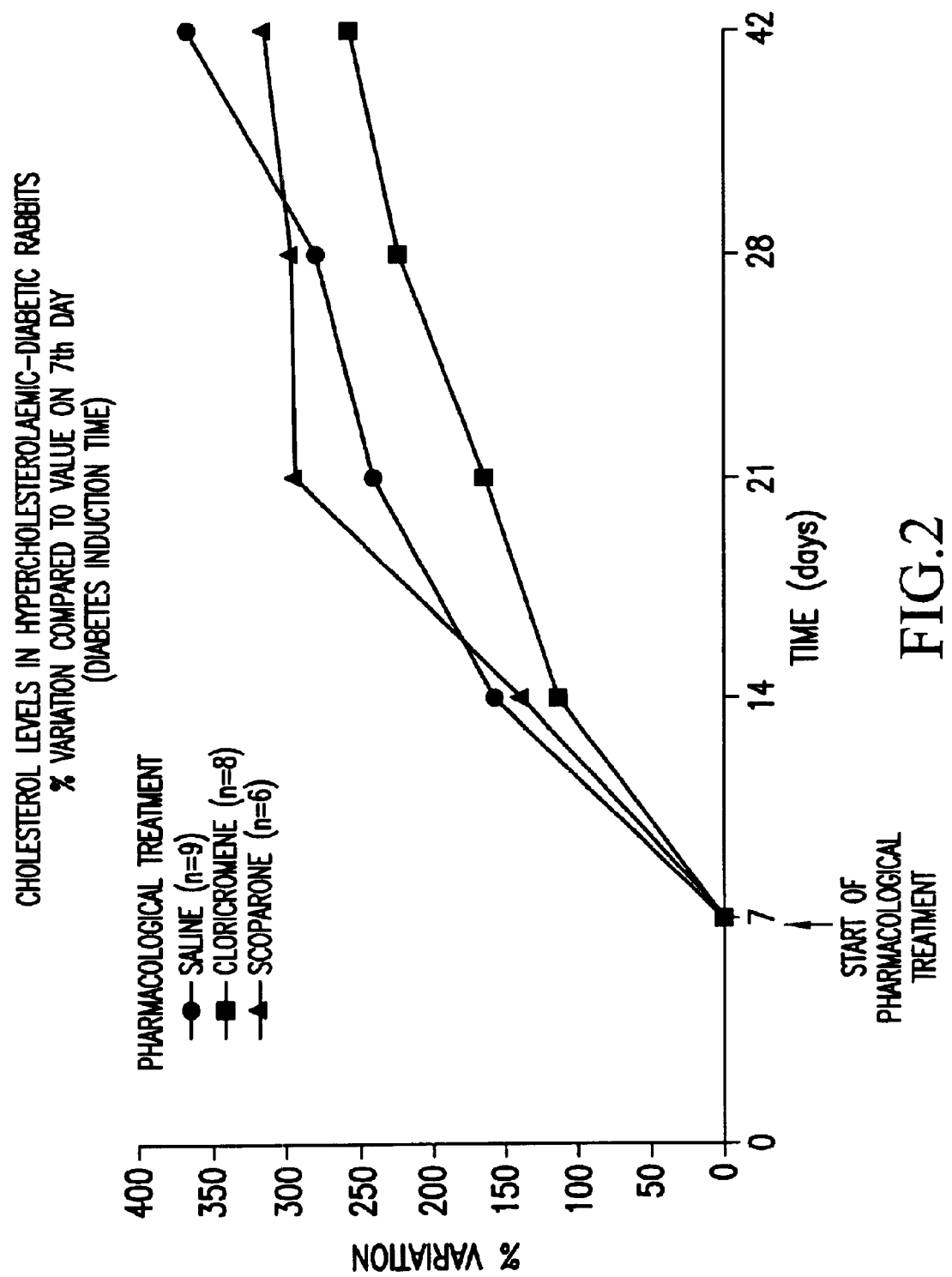
FIG. 2 shows the % variation of cholesterol levels in hypercholesterolaemic-diabetic rabbits from the $7^{th}$ day and beyond in rabbits treated with cloricromene, scoparone, or saline.

In the same experimental model, in which a diabetic pathology is induced by treating the animals with alloxan, and hypercholesterolaemia is induced by administering a 1% cholesterol diet, we monitored at weekly intervals the cholesterol levels of the rabbits, which had been divided into the following treatment groups:
1. Control, treated with saline solution
2. Scoparone
3. Cloricromene The results reported in FIG. 2 show that cholesterol levels in the group of animals treated with cloricromene are markedly lower than those of both the control group and that treated with scoparone. The difference is evident as early as the third week of treatment. In this experiment, as in the previous one, the product proved to be practically free from any toxic effects: indeed, at the end of the experiment, the number of animals that completed the treatment with scoparone was considerably lower than the number of those treated with cloricromene.

Test No. 3

Figure 3:
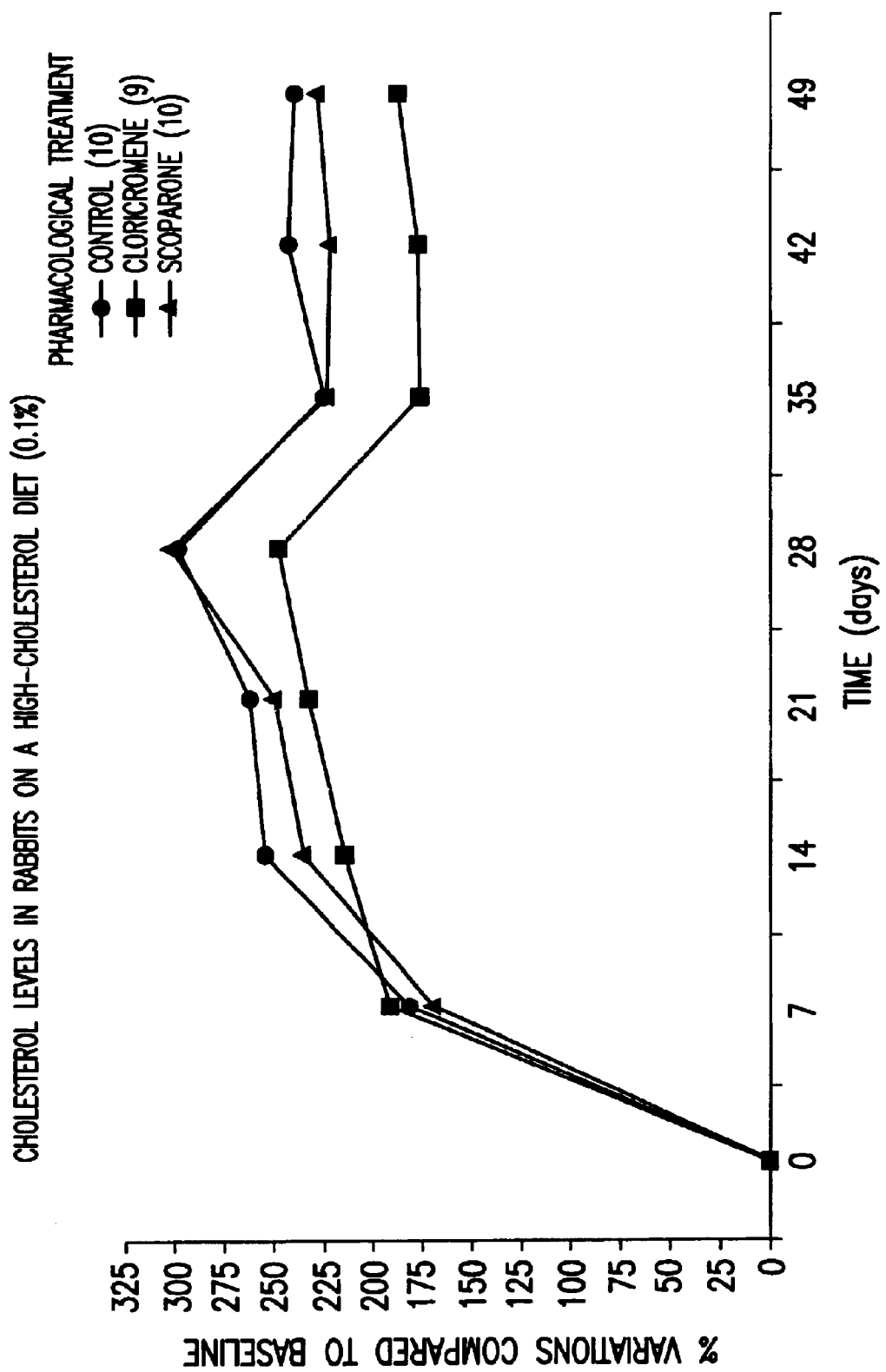
FIG. 3 shows the cholesterol levels in rabbits on a high-cholesterol diet.

As further confirmation of this interesting result, we prepared another experimental model. In this case, hypercholesterolaemia was induced in rabbit by administration of a 0.1% cholesterol diet, without simultaneously inducing diabetes. In these experimental conditions, cholesterol levels of around 250 mg/dl were obtained, that is to say, values that are compatible with the pathological situation normally observed in humans affected by hypercholesterol. The rabbits were divided into three treatment groups: controls treated with saline, a second group receiving scoparone and a third receiving cloricromene. The results in this case too showed that cholesterol levels were markedly lower in the group treated with cloricromene than in the control group that received no treatment and in the group of animals which received scoparone (FIG. 3).

Cholesterol-Lowering and Antithrombotic Effects of Cloricromene

We conducted a multicentre, double-blind, randomised study, controlled versus placebo, on 159 patients with Peripheral Vascular Disease (PVD) at Fontaine stage II, the classic symptom of which is Intermittent Claudication (IC).

PVD is a pathology involving thrombotic risk, and IC patients run a two- to fivefold greater risk of cardiovascular ischemic diseases than other subjects, with a particularly high mortality rate from myocardial infarct, stroke and thrombosis.

Hypercholesterolaemia is beyond doubt one of the risk factors in the genesis of the atherosclerotic processes that lead to the formation of atheromatous plaques.

It has also been demonstrated that vessel walls altered by atheromatous plaques may give rise to interactions of the endothelium with the circulating cells (mainly platelets and leukocytes) that trigger the thrombotic process.

In our study, besides assessing the effect of cloricromene on IC, we also studied the cholesterol-lowering effects of the drug and the incidence of major cardiovascular events (myocardial infarction, stroke, vascular death, progression to Fontaine stages III–IV) after a treatment period of six months.

In analysing the cholesterol-lowering effect, 117 patients were considered who presented cholesterol values at baseline of over 190 mg/dI.

The critical value of 190 mg/dl was selected on the basis of data from the international literature that report this value as the risk threshold in pathologies such as cardiac ischaemia and atherosclerosis in general, in which excessive cholesterol represents a real risk factor. Therefore, the patients who presented cholesterol values equal to or over 190 mg/dl were considered to be at risk from said pathologies.

For the purposes of this analysis, 58 patients were treated for 6 months with 200 mg of cloricromene per day (one capsule of 100 mg twice a day), while the remaining 59 patients were treated with placebo (Table). All the patients also took aspirin at a dose of 160 mg/day throughout the trial.

TABLE

| Group | Cholesterol levels at Week 0 | Cholesterol levels at week 24 | p |
|---|---|---|---|
| Group treated with Cloricromene | 243 ± 31 | 229 ± 32 | p = 0.0035 |
| Placebo group | 234 ± 30 | 234 ± 39 | p = ns | ns = not significant

From analysis of the covariance, the estimation of the difference between the treatment groups proves statistically significant in favour of the group treated with cloricromene (p=0.04, with a value of α=0.05).

As regards the onset of severe events, no major cardiovascular events or deaths were observed in either group.

The results suggest that cloricromene may be useful in controlling thrombotic risk, by lowering cholesterol levels and inhibiting cellular interactions (endothelial cells, platelets, leukocytes) which might otherwise contribute towards the formation of thrombi, with the subsequent risk of major cardiovascular events.

FORMULATION EXAMPLES

| Capsules | |
|---|---|
| Cloricromene | 100 mg |
| Saccharose | 92.77 mg |
| Maize starch | 30.93 mg |

-continued

| | |
|---|---|
| Magnesium stearate | 34.6 mg |
| Povidone | 25.48 mg |
| Monobasic potassium phosphate | 20.8 mg |
| Cellulose acetate | 95.42 mg |
| Gelatin container | 77 mg |
| Injectable composition | |
| Cloricromeme hydrochloride | 30 mg |
| Mannitol | 30 mg |
| Sodium chloride | 45 mg |
| Water for injection | 5 ml |

The formulations being thus described in detail, it is obvious that they can be modified in various ways. Such modifications are not to be considered as variations from the spirit and purpose of the invention, and any such modification which may appear obvious to an expert in the specific sector are to be considered as coming within the scope of the following claims.

What is claimed is:

1. A method of treating hypercholesterolaemia in a patient in need thereof comprising administering to said patient a pharmaceutically acceptable amount of a composition comprising cloricromene or a cloricromene salt thereof.

2. The method of claim 1, wherein the composition has cholesterol-lowering activity.

3. The method of claim 1, wherein the composition has cholesterol-lowering antithrombotic activity.

4. The method of claim 3, wherein the composition has activity in a patient with cholesterol levels in the plasma of over 190 mg/dl.

5. The method according to any one of claims 1–4, wherein the pharmaceutical composition is in the form of a capsule, a tablet, an injectable solution, or a transdermal system.

6. The method according to claim 1, wherein the composition comprises a cloricromene salt.

* * * * *